(12) United States Patent
Althenayan

(10) Patent No.: US 10,919,825 B2
(45) Date of Patent: *Feb. 16, 2021

(54) MEMBRANE-BASED PROCESS FOR BUTANOLS PRODUCTION FROM MIXED BUTENES

(71) Applicant: Saudi Arabian Oil Company, Dhahran (SA)

(72) Inventor: Faisal M. Althenayan, Dhahran (SA)

(73) Assignee: SAUDI ARABIAN OIL COMPANY

(*) Notice: Subject to any disclaimer, the term of this patent is extended or adjusted under 35 U.S.C. 154(b) by 0 days.

This patent is subject to a terminal disclaimer.

(21) Appl. No.: 16/739,993

(22) Filed: Jan. 10, 2020

(65) Prior Publication Data

US 2020/0189996 A1  Jun. 18, 2020

Related U.S. Application Data

(63) Continuation of application No. 16/218,008, filed on Dec. 12, 2018, now Pat. No. 10,570,071.

(51) Int. Cl.
*B01J 19/00* (2006.01)
*B01J 19/24* (2006.01)
(Continued)

(52) U.S. Cl.
CPC ............ *C07C 29/04* (2013.01); *B01J 19/2475* (2013.01); *C07C 29/88* (2013.01); *C07C 31/12* (2013.01); *B01J 19/244* (2013.01)

(58) Field of Classification Search
CPC ........ B01D 63/00; B01D 63/06; C07C 29/00; C07C 29/03; C07C 29/04; C07C 29/74;
(Continued)

(56) References Cited

U.S. PATENT DOCUMENTS 3,370,102 A  2/1968 Leroy et al.
3,819,742 A  6/1974 Bulvestre et al.
(Continued)

FOREIGN PATENT DOCUMENTS

GB  2072668 B  10/1981
WO  2006069991 A2  7/2006
(Continued)

*Primary Examiner* — Natasha E Young
(74) *Attorney, Agent, or Firm* — Bracewell LLP; Constance R. Rhebergen

(57) ABSTRACT

A method of separately producing tert-butanol and sec-butanol, comprising the steps of introducing a mixed butenes stream to a tube side of a reaction membrane unit, introducing a TBA reactor water feed to the tube side of the reaction membrane unit, introducing a sweep gas to a shell side of the reaction membrane unit, introducing an SBA reactor water feed to the shell side, allowing the mixed butenes stream to contact the tube side of a such that selective gases in the mixed butenes stream permeate through the membrane to the shell side, allowing the selective gases that permeate through the membrane to react with water to produce sec-butanol, allowing retentate gases that fail to permeate through the membrane to react with water to produce tert-butanol, collecting the tert-butanol in a TBA reactor effluent, and collecting the sec-butanol in a SBA reactor effluent.

20 Claims, 4 Drawing Sheets

(51) Int. Cl.
  *C07C 29/04*   (2006.01)
  *C07C 29/88*   (2006.01)
  *C07C 31/12*   (2006.01)
  *B01D 3/06*   (2006.01)

(58) Field of Classification Search
  CPC ......... C07C 29/88; C07C 31/00; C07C 31/02;
        C07C 31/12; B01J 19/00; B01J 19/24;
        B01J 19/2415; B01J 19/244; B01J
                              19/2475
  See application file for complete search history.

(56) References Cited

U.S. PATENT DOCUMENTS

| | | |
|---|---|---|
| 4,065,512 A | 12/1977 | Cares |
| 4,699,892 A | 10/1987 | Suzuki |
| 4,876,403 A | 10/1989 | Cohen et al. |
| 5,146,009 A | 9/1992 | Cohen et al. |
| 5,672,782 A | 9/1997 | Hattori et al. |
| 5,763,685 A | 6/1998 | Kruse et al. |
| 7,141,707 B2 | 11/2006 | Beckmann et al. |
| 7,749,414 B2 | 7/2010 | Bitterlich et al. |
| 8,865,950 B2 | 10/2014 | Abba et al. |
| 8,921,619 B2 * | 12/2014 | Harale ................ B01J 19/2475 568/895 |
| 9,199,214 B2 | 12/2015 | Harale et al. |
| 10,570,071 B1 * | 2/2020 | Althenayan ............. C07C 29/04 |
| 2005/0242031 A1 | 11/2005 | Reusch et al. |
| 2009/0118551 A1 | 5/2009 | Buijs et al. |
| 2010/0048960 A1 | 2/2010 | Degen et al. |
| 2010/0276368 A1 | 11/2010 | Gonzalez et al. |
| 2012/0142865 A1 | 6/2012 | Balsara et al. |
| 2013/0041186 A1 | 2/2013 | Abba et al. |
| 2013/0144088 A1 | 6/2013 | Harale et al. |
| 2014/0039226 A1 | 2/2014 | Xu et al. |
| 2014/0066667 A1 | 3/2014 | Arjah et al. |
| 2014/0360938 A1 | 12/2014 | Hayashi et al. |
| 2015/0225320 A1 | 8/2015 | Shaik et al. |

FOREIGN PATENT DOCUMENTS

| | | |
|---|---|---|
| WO | 2013085964 A2 | 6/2013 |
| WO | 2015123026 A1 | 8/2015 |

* cited by examiner

MEMBRANE-BASED PROCESS FOR BUTANOLS PRODUCTION FROM MIXED BUTENES

CROSS-REFERENCE TO RELATED APPLICATIONS

This patent application is a continuation of U.S. Non-Provisional application Ser. No. 16/218,008 filed on Dec. 12, 2018, and issued as U.S. Pat. No. 10,570,071 on Feb. 25, 2020. For purposes of United States patent practice, the non-provisional application is incorporated by reference in its entirety.

TECHNICAL FIELD

Disclosed are methods for upgrading petroleum. Specifically, disclosed are methods and systems for upgrading petroleum using pretreatment processes.

BACKGROUND

A butenes stream from a refinery can include mixed butene isomers, such as 1-butene, cis-2-butene, trans-2-butene, and iso-butene. A butenes stream is often inexpensive and thus processes seek to convert the compounds to more valuable chemicals, such as butanols. Not all refineries produce a mixed butenes, so processes to convert the isomers to more valuable compounds are limited. Butanols are of greater value than butenes because of their various uses. Butanols can include sec-butanol (SBA) and tert-butanol (TBA). TBA can be used as a fuel additive and SBA can be used as a solvent. Alternately, SBA can be converted to butanone, also known as methyl ethyl ketone (MEK).

In certain processes, butanols can be produced together from mixed butene isomers in one step processes. However, thermodynamic limitations can impact the products produced. The temperature of the reaction influences the butanol produced, increased temperatures favor production of SBA over TBA, while inversely reduced temperatures favor production of TBA over SBA.

SUMMARY

Disclosed are methods for upgrading petroleum. Specifically, disclosed are methods and systems for upgrading petroleum using pretreatment processes.

In a first aspect, a method of separately producing tert-butanol and sec-butanol is provided. The method includes the steps of introducing a mixed butenes stream to a tube side of a reaction membrane unit, where the tube side of the reaction membrane unit includes a TBA catalyst, where the mixed butenes stream includes butene gases, introducing a TBA reactor water feed to the tube side of the reaction membrane unit, where the TBA reactor water feed includes water, introducing a sweep gas to a shell side of the reaction membrane unit, where the sweep gas is selected from the group consisting of nitrogen, argon, other noble gases, and combinations of the same, where the shell side of the reaction membrane unit includes an SBA catalyst, introducing an SBA reactor water feed to the shell side of the reaction membrane unit, where the SBA reactor water feed includes water, allowing the mixed butenes stream to contact the tube side of a membrane in the reaction membrane unit such that selective gases in the mixed butenes stream permeate through the membrane to the shell side, where the selective gases are selected from the group consisting of 1-butene, 2-butene, and combinations of the same, allowing the selective gases that permeate through the membrane to react with water in the presence of the SBA catalyst to produce sec-butanol, where the shell side operates at a SBA reaction temperature, allowing retentate gases that fail to permeate through the membrane to react with water in the presence of the TBA catalyst to produce tert-butanol, where the shell side operates at a TBA reaction temperature, where the retentate gases include isobutene, collecting the tert-butanol in a TBA reactor effluent, and collecting the sec-butanol in a SBA reactor effluent.

In certain aspects the method further includes the steps of introducing the SBA reactor effluent to an SBA gases splitter, where the SBA gases splitter is configured to separate unreacted gases from the SBA reactor effluent, separating unreacted gases from the SBA reactor effluent to produce an unreacted gases stream and a product liquid stream, introducing the product liquid stream to a SBA liquid separator, where the SBA liquid separator is configured to separate water from the product liquid stream, and separating water from the product liquid stream to produce a separated water stream and an SBA product stream. In certain aspects the method further includes the steps of introducing the TBA reactor effluent to a TBA gases splitter, where the TBA gases splitter is configured to separate unreacted butenes from the TBA reactor effluent, separating the unreacted butenes from the TBA reactor effluent to produce an unreacted butenes stream and a separated liquids stream, introducing the separated liquids stream to a TBA liquid separator, where the TBA liquid separator is configured to separate water from the separated liquids stream, and separating water from the product liquid stream to produce a recycled water stream and a TBA product stream. In certain aspects, the SBA catalyst is selected from the group consisting of organic acids, inorganic acids, and solid acids. In certain aspects, the TBA catalyst is selected from the group consisting of organic acids, inorganic acids, and solid acids. In certain aspects, the SBA reaction temperature is between 80 deg C. and 250 deg C. In certain aspects, the TBA reaction temperature is between 5 deg C. and 120 deg C.

In a second aspect, a method of separately producing tert-butanol and sec-butanol is provided. The method includes the steps of introducing a mixed butenes stream to a shell side of a reaction membrane unit, where the shell side of the reaction membrane unit includes a TBA catalyst, where the mixed butenes stream includes butene gases, introducing a TBA reactor water feed to the shell side of the reaction membrane unit, introducing a sweep gas to a tube side of the reaction membrane unit, where the sweep gas is selected from the group consisting of nitrogen, argon, other noble gases, and combinations of the same, allowing the mixed butenes stream to contact the shell side of a membrane in the reaction membrane unit such that selective gases in the mixed butenes stream permeate through the membrane to the tube side, where the selective gases are selected from the group consisting of 1-butene, 2-butene, and combinations of the same, collecting the selective gases in the sweep gas to produce the permeate stream, allowing retentate gases that fail to permeate through the membrane to react with water in the presence of the TBA catalyst to produce tert-butanols, where the shell side operates at a TBA reaction temperature, where the retentate gases include isobutene, collecting the TBA in a TBA reactor effluent, introducing the permeate stream to a sec-butanol (SBA) reactor, introducing an SBA reactor water feed to the SBA reactor, where the SBA reactor water feed includes water, where the SBA reactor includes an SBA catalyst, where the SBA catalyst is configured to catalyze a reaction of 1-butene and 2-butene with water to produce sec-butanol, reacting the permeate stream with the SBA reactor water feed in the SBA reactor to produce a SBA reactor effluent, where the SBA reactor effluent includes sec-butanol, where the SBA reactor operates at a SBA reaction temperature, and introducing the retentate stream to a tert-butanol (TBA) reactor.

In a third aspect, a method of separately producing sec-butanol and tert-butanol, the method includes the steps of introducing a mixed butenes stream to a shell side of a separation membrane unit, where the mixed butenes stream includes butene gases, introducing a sweep gas to a tube side of the separation membrane unit, where the sweep gas is selected from the group consisting of nitrogen, argon, other noble gases, and combinations of the same, allowing the mixed butenes stream to contact the shell side of a membrane in the separation membrane unit such that selective gases in the mixed butenes stream permeate through the membrane to the tube side, where the selective gases are selected from the group consisting of 1-butene, 2-butene, and combinations of the same, collecting the selective gases in the sweep gas to produce the permeate stream, collecting retentate gases that fail to permeate through the membrane gases to produce a retentate stream, where the retentate gases include isobutene, introducing the permeate stream to a sec-butanol (SBA) reactor, introducing an SBA reactor water feed to the SBA reactor, where the SBA reactor water feed includes water, where the SBA reactor includes an SBA catalyst, where the SBA catalyst is configured to catalyze a reaction of 1-butene and 2-butene with water to produce sec-butanol, reacting the permeate stream with the SBA reactor water feed in the SBA reactor to produce a SBA reactor effluent, where the SBA reactor effluent includes sec-butanol, where the SBA reactor operates at a SBA reaction temperature, introducing the retentate stream to a tert-butanol (TBA) reactor, introducing a TBA reactor water feed to the TBA reactor, where the TBA reactor water feed includes water, where the TBA reactor includes a TBA catalyst, where the TBA catalyst is configured to catalyze a reaction of isobutene with water to produce tert-butanol, and reacting the retentate stream with the TBA reactor water feed in the TBA reactor to produce a TBA reactor effluent, where the TBA reactor effluent includes tert-butanol, where the TBA reactor operates at a TBA reaction temperature.

BRIEF DESCRIPTION OF THE DRAWINGS

These and other features, aspects, and advantages of the scope will become better understood with regard to the following descriptions, claims, and accompanying drawings. It is to be noted, however, that the drawings illustrate only several embodiments and are therefore not to be considered limiting of the scope as it can admit to other equally effective embodiments.

In the accompanying Figures, similar components or features, or both, may have a similar reference label.

DETAILED DESCRIPTION

While the scope of the apparatus and method will be described with several embodiments, it is understood that one of ordinary skill in the relevant art will appreciate that many examples, variations and alterations to the apparatus and methods described here are within the scope and spirit of the embodiments.

Accordingly, the embodiments described are set forth without any loss of generality, and without imposing limitations, on the embodiments. Those of skill in the art understand that the scope includes all possible combinations and uses of particular features described in the specification.

Figure 1:
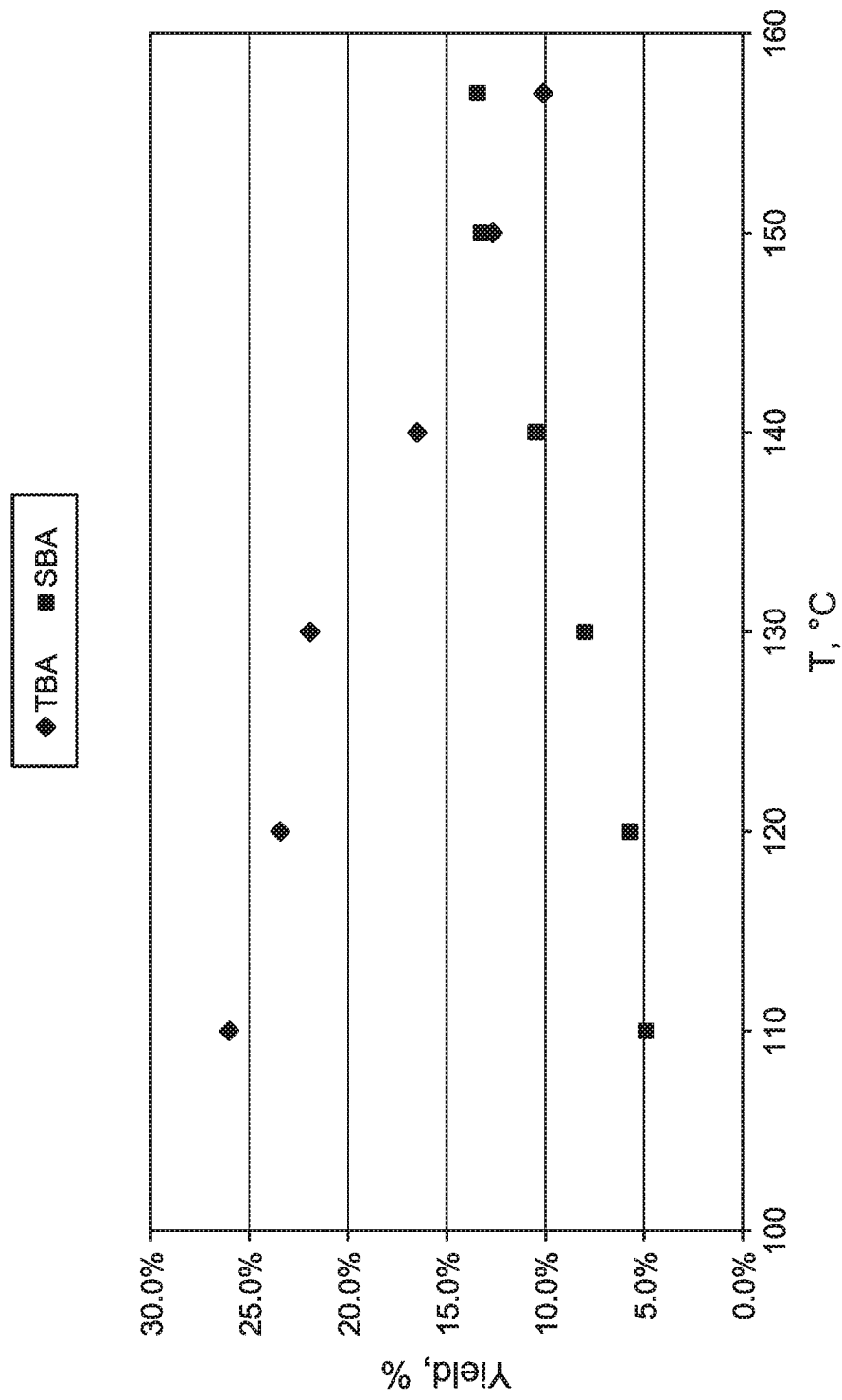
FIG. 1 is a graph of the relationship between temperature and butanol yield for a given butene stream composition.

The processes and systems described are directed to processes for separately producing sec-butanol (SBA) and tert-butanol (TBA). The processes and systems described provide for separating butenes and separately hydrating the butenes to produce butanols. Advantageously, separately hydrating butenes provides a process and system which can optimize reaction temperatures for the separated butenes and thus increase production of butanols. Temperature impacts which butanol is produced. For a given composition of a butene stream, as shown in table 1, the production of TBA is favored at lower temperatures but the production of SBA is favored at higher temperatures, as shown in FIG. 1.

TABLE 1

Typical composition of a butenes stream from a refinery

| Compound | Composition, mol % |
|---|---|
| 1-butene | 21 |
| Cis-2-butene | 19 |
| Trans-2-butene | 25 |
| Iso-butene | 35 |

Higher temperatures are required for conversion of 1-butene and 2-butene to SBA because those compounds are not as reactive, requiring higher temperatures to initiate the reactions. At temperatures between 5 deg C. and 120 deg C., 1-butene remains unreacted or has a low reactivity rate, however, the reactivity of 1-butene increases as the temperature increases with an economically optimal range of 80 deg C. to 250 deg C. Advantageously, the separate production of SBA and TBA can be accomplished by combining the step of separating butenes and hydrating the butenes in one unit. Advantageously, the described process and systems provide a simple system to separate feed streams for sec-butanol and tert-butanol production. Advantageously, the described process and systems increase overall butene conversion by optimizing the reaction temperature and as a result increase overall butanol production. Advantageously, the described process and systems can reduce energy consumption as compared to conventional systems to produce butanols. Advantageously, the described process and system produces separate streams of sec-butanol and tert-butanol which can maximize the value of the butanols. Advantageously, separating butene isomers requires less complexity than the separation of butanols. Advantageously, the described process and systems allow for targeted catalysts to be used in each of the reactors, one catalyst for SBA and one for TBA, rather than a combined catalyst that catalyzes both hydration reactions.

As used throughout, "hydration reaction" refers to a reaction where an unsaturated compound reacts with water, typically to produce an alcohol.

As used throughout, "selective for" refers to gases that can permeate a membrane. For example, a membrane that is selective for 1-butene, means the membrane is designed to allow 1-butene to permeate the membrane.

As used throughout, "2-butene" refers to both cis-2-butene and trans-2-butene, unless otherwise indicated.

As used throughout, "tert-butanol" is also known as tert-butyl alcohol or t-butanol with the formula $(CH_3)_3COH$.

As used throughout, "sec-butanol" is also known as 2-butanol with the formula $CH_3CH(OH)CH_2CH_3$.

As used throughout,"

The following embodiments, provided with reference to the figures, describe the upgrading process.

Figure 2:
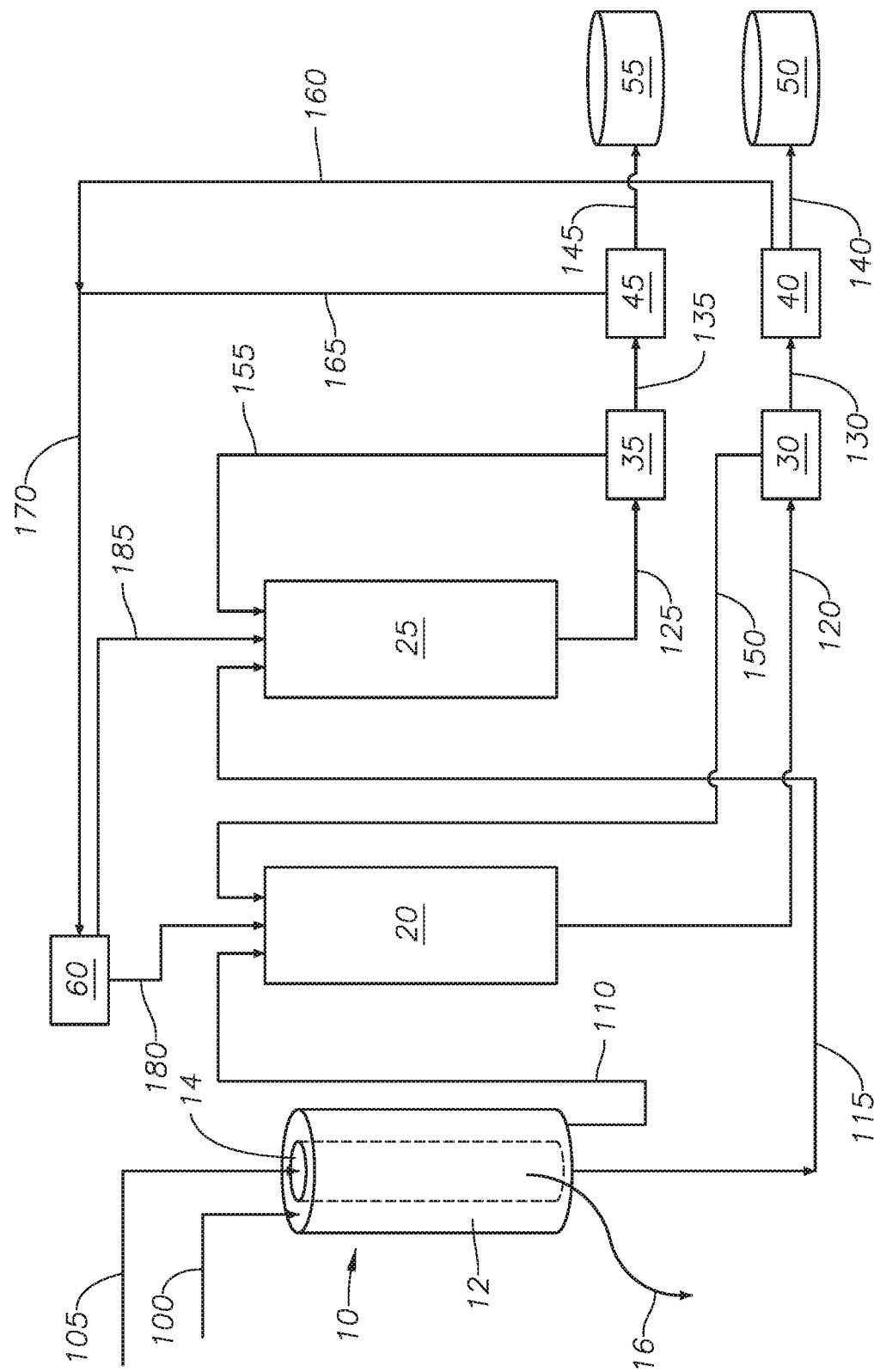
FIG. 2 provides a process flow diagram of an embodiment of the process.

Referring to FIG. 2, a process flow diagram of a butanol process is provided. Mixed butenes stream 100 can be introduced to shell side 12 of separation membrane unit 10. Mixed butenes stream 100 can include butene gases. The butene gases can include isobutene, 1-butene, 2-butene, and combinations of the same. The 2-butene can include cis-2-butene, trans-2-butene, and combinations of the same. Mixed butenes stream 100 can be in the absence of dienes, such as butadiene and pentadiene.

Separation membrane unit 10 can include shell side 12, tube side 14, and membrane 16. Membrane 16 can be a cylinder defining a space extending through a longitudinal direction of membrane 16. Membrane 16 can define tube side 14, such that tube side 14 is enclosed within membrane 16 and can be the space defined by membrane 16. Membrane 16 and tube side 14 can extend the length of shell side 12. Shell side 12 can be an annulus defined by a wall of separation membrane unit 10 and membrane 16, such that mixed butenes stream 100 can flow through the annulus. Alternately, separation membrane unit 10 can be arranged such that tube side 14 forms one layer and shell side 12 forms a second layer with the two layers separated by membrane 16 (not shown).

The temperature in separation membrane unit 10 can be between −100 deg C. and 250 deg C. and alternately between 5 deg C. and 160 deg C. The pressure on the retentate side, shell side 12, of separation membrane unit 10 can be between 0.1 MPa and 10 MPa and alternately between 0.1 MPa and 7 MPa. The pressure on the permeate side, tube side 14, of separation membrane unit 10 can be between 0.01 MPa and 5 MPa and alternately between 0.1 MPa and 3 MPa. The pressure on the retentate side of separation membrane unit 10 can be greater than the pressure on the permeate side. According to the process embodied in FIG. 2, shell side 12 forms the retentate side and tube side 14 forms the permeate side of separation membrane unit 10.

Membrane 16 can be any type of membrane selective for one or more of the butene gases in mixed butenes stream. One of skill in the art can appreciate that membrane composition is selected specifically for the components to be separated and the composition of a feed. By way of example, a membrane that can separate one component from a feed containing three components could separate two components from a feed containing four components. Membrane 16 can be composed of one or more layers allowing for transport of gases. The layers of membrane 16 can be composed of metal oxides, sintered metal compounds, zeolites, and combinations of the same. Membrane 16 can include aluminum, gallium, silicon, germanium, titanium, zirconium, magnesium, oxygen, and combinations of the same. Membrane 16 can include alumina, silicon dioxide, aluminosilicate, titanium dioxide, zirconium dioxide, magnesium oxide, and combinations of the same. The zeolites can include MFI-type zeolites, CaA-type zeolite, ZSM-5-type zeolite, Membrane 16 or the layers of membrane 16 can have a molecular sieve structure. Membrane 16 can allow selective gases to permeate. The selective gases can include 1-butene and alternately 1-butene and 2-butene. In at least one embodiment, membrane 16 is selective for 1-butene and the selective gases includes 1-butene. In at least one embodiment, membrane 16 is selective for 2-butene and the selective gases includes 2-butene. In at least one embodiment, membrane 16 is selective for both 1-butene and 2-butene and the selective gases includes 1-butene and 2-butene. In separation membrane unit 10, the selective gases in mixed butenes stream 100 can permeate from shell side 12 through membrane 16 to tube side 16. Advantageously, the use of membranes provides a method for selective separation on a molecular level, allowing separation of components that cannot be separated by conventional separation methods. Advantageously, membranes are low energy and does not require phase change in order to separate the components.

Sweep gas 105 can be introduced to tube side 14 of separation membrane unit 10. Sweep gas 105 can contain any inert gas. Examples of sweep gas 105 include nitrogen, argon, other noble gases, and combinations of the same. The selective gases that permeate to tube side 14 can be collected in sweep gas 105 and exit separation membrane unit 10 as permeate stream 115.

The butene gases in mixed butenes 100 that do not permeate through membrane 16 remain in shell side 12 as retentate gases. The retentate gases can include 1-butene, alternately, 1-butene and 2-butene, and alternately isobutene. In at least one embodiment, the retentate gases include isobutene. The retentate gases exit separation membrane unit 10 as retentate stream 110.

Retentate stream 110 can be introduced to tert-butanol (TBA) reactor 20. TBA reactor water feed 180 can be introduced to TBA reactor 20. TBA reactor water feed 180 can include water.

TBA reactor 20 can be any type of reactor capable of supporting a catalytic reaction. Reactors suitable for use as TBA reactor 20 can include batch reactors, semi-batch reactors, and continuous reactors. Examples of reactors suitable for use as TBA reactor 20 include fixed bed reactors, plug flow reactors (PFR), a continuously stirred tank reactor (CSTR), and a reaction vessel with agitation. TBA reactor 20 can be operated at a TBA reaction temperature. The TBA reaction temperature can be between 5 deg C. and 120 deg C. TBA reactor 20 can be operated a pressure between 1 bar (100 kiloPascals (kPa)) and 100 bar (10000 kPa) atmospheric pressure. TBA reactor 20 can be operated a residence time between 0.01 hours and 20 hours. TBA reactor 20 can include a TBA catalyst. Commonly owned U.S. patent application Ser. No. 13/977,860, which is hereby incorporated by reference in its entirety, sets forth catalysts that can be used as catalysts for use as the TBA catalyst. Examples of the TBA catalyst include organic acids, inorganic acids, and solid acids. The organic acids can include acetic acid, tosylate acid, perfluorinated acetic acid, and combinations of the same. The inorganic acids can include heteropoly acids, hydrochloric acid (HCl), phosphoric acid ($H_3PO_4$), sulfuric acid ($H_2SO_4$), and combinations of the same. The solid acids can include ion exchange resins, zeolites, and inorganic supported acids.

The retentate gases in retentate stream 110 can react with water in TBA reactor water feed 180 to produce TBA reactor effluent 120. The reaction between the retentate gases and the water can be catalyzed by the TBA catalyst. The reaction between the retentate gases and the water can produce tert-butanol. TBA reactor effluent 120 can include tert-butanol, butenes, water, and combinations of the same. TBA reactor effluent 120 can be introduced to TBA gases splitter 30. In at least one embodiment, the temperature of TBA reactor effluent 120 can be cooled in a heat exchanger before being introduced to TBA gases splitter 30.

TBA gases splitter 30 can be any type of separation unit capable of separating gases from liquids. TBA gases splitter 30 can be a high pressure cold separator, a hot separator, a flash separation device, or a separation unit in the absence of a flash zone. Examples of a flash separation device include a flash drum. Examples of a separation unit in the absence of a flash zone can include a cyclonic phase separation device, a splitter, and separation device based on physical separation or mechanical separation of vapors and liquids. TBA gases splitter 30 can include one or more separation units.

TBA gases splitter 30 can separate unreacted butenes. Unreacted butenes can include isobutene, 2-butene, and combinations of the same. The unreacted butenes can leave TBA gases splitter 30 as unreacted butenes stream 150. Unreacted butene stream 150 can be recycled to TBA reactor 20. The operating conditions of TBA gases splitter 30 can be based on the type of separator employed and the desired separation.

The remaining liquids can be removed as separated liquids stream 130. Separated liquids stream 130 can include tert-butanol, water, and combinations of the same. Separated liquids stream 130 can be introduced to TBA liquid separator 40.

TBA liquid separator 40 can be any type of separation unit capable of separating water from butanol. Examples of TBA liquid separator 40 can include gas stripping, vacuum flash, liquid-liquid extraction, liquid-vapor separation, supercritical extraction, membrane solvent extraction, membrane pervaporation, adsorption, and combinations of the same. Separation in TBA liquid separator 40 can be based on distillation, azeotropic distillation, extractive distillation, and membrane-based separation. Extractive distillation methods can include liquid solvents or dissolved salts. Membrane-based separation methods can include ultra-filtration, reverse osmosis, total vaporization of the liquid, or partial vaporization of the liquid. TBA liquid separator 40 can include one or more units, one or more stages, or one or more devices. The separated water can be withdrawn as recycled water stream 160. Recycled water stream 160 can be further treated, can be recycled to the front end of the process, or can be disposed. In at least one embodiment, recycled water stream 160 can be mixed with separated water stream 165 to produce mixed recycled water 170. Mixed recycled water 170 can be introduced to water storage tank 60.

The tert-butanol can be withdrawn from TBA liquid separator 40 as TBA product stream 140. TBA product stream 140 can be further treated and alternately can be introduced to TBA storage tank 50.

Permeate stream 115 can be introduced to sec-butanol (SBA) reactor 25. SBA reactor water feed 185 can be introduced to SBA reactor 25. SBA reactor water feed 185 can include water.

SBA reactor 25 can be any type of reactor capable of supporting a catalytic reaction. Reactors suitable for use as TBA reactor 20 can include batch reactors, semi-batch reactors, and continuous reactors. Examples of reactors suitable for use as TBA reactor 20 include fixed bed reactors, plug flow reactors (PFR), a continuously stirred tank reactor (CSTR), and a reaction vessel with agitation. SBA reactor 25 can be operated at a SBA reaction temperature. The SBA reaction temperature can be between 80 deg C. and 250 deg C. At temperatures below 80 deg C., the reaction to produce SBA is not as effectively catalyzed reducing the yield of SBA. At temperatures greater than 250 deg C. oligomerization can occur and catalyst reactivity declines. SBA reactor 25 can be operated a pressure between 1 bar (100 kiloPascals (kPa)) and 100 bar (10000 kPa) atmospheric pressure. SBA reactor 25 can include a SBA catalyst. Commonly owned U.S. patent application Ser. No. 13/977,860, which is hereby incorporated by reference in its entirety, sets forth catalysts that can be used as catalysts for use as the SBA catalyst. Examples of the SBA catalyst include organic acids, inorganic acids, and solid acids. The organic acids can include acetic acid, tosylate acid, perfluorinated acetic acid, and combinations of the same. The inorganic acids can include heteropoly acids, hydrochloric acid (HCl), phosphoric acid ($H_3PO_4$), sulfuric acid ($H_2SO_4$), and combinations of the same. The solid acids can include ion exchange resins, zeolites, and inorganic supported acids.

The selective gases in permeate stream 115 can react with water in SBA reactor water feed 185 to produce SBA reactor effluent 125. The reaction between the selective gases and the water can be catalyzed by the SBA catalyst. The reaction between the selective gases and the water can produce sec-butanol. SBA reactor effluent 125 can include sec-butanol, butenes, water, and combinations of the same. SBA reactor effluent 125 can be introduced to SBA gases splitter 35. In at least one embodiment, the temperature of SBA reactor effluent 125 can be cooled in a heat exchanger before being introduced to SBA gases splitter 35.

SBA gases splitter 35 can be any type of separation unit capable of separating gases from liquids. SBA gases splitter 35 can be a high pressure cold separator, a hot separator, a flash separation device, or a separation unit in the absence of a flash zone. Examples of a flash separation device include a flash drum. Examples of a separation unit in the absence of a flash zone can include a cyclonic phase separation device, a splitter, and separation device based on physical separation or mechanical separation of vapors and liquids. SBA gases splitter 35 can include one or more separation units. SBA gases splitter 35 can separate unreacted gases. The unreacted gases can include 1-butene, 2-butene, and combinations of the same. The unreacted gases can leave SBA gases splitter 35 as unreacted gases stream 155. Unreacted gases stream 155 can be recycled to SBA reactor 25. The operation conditions of SBA gases splitter 35 can be based on the type of separator employed and the desired separation.

The remaining liquids can removed as separated liquids stream 135. Separated liquids stream 135 can include sec-butanol, water, and combinations of the same. Separated liquids stream 135 can be introduced to SBA liquid separator 45.

SBA liquid separator 45 can be any type of separation unit capable of separating water and butanols. SBA liquid separator 45 can be a high pressure cold separator, a hot separator, a flash separation device, or a separation unit in the absence of a flash zone. Examples of a flash separation device include a flash drum. Examples of a separation unit in the absence of a flash zone can include a cyclonic phase separation device, a splitter, and separation device based on physical separation or mechanical separation of vapors and liquids. SBA liquid separator 45 can include one or more separation units. The separated water can be withdrawn as separated water stream 165. Separated water stream 165 can be further treated, can be recycled to the front end of the process, or can be disposed. In at least one embodiment, separated water stream 165 can be mixed with recycled water stream 160 to produce mixed recycled water 170. The sec-butanol can be withdrawn from SBA liquid separator 45 as SBA product stream 145. SBA product stream 145 can be further treated and alternately can be introduced to SBA storage tank 55.

Figure 3:
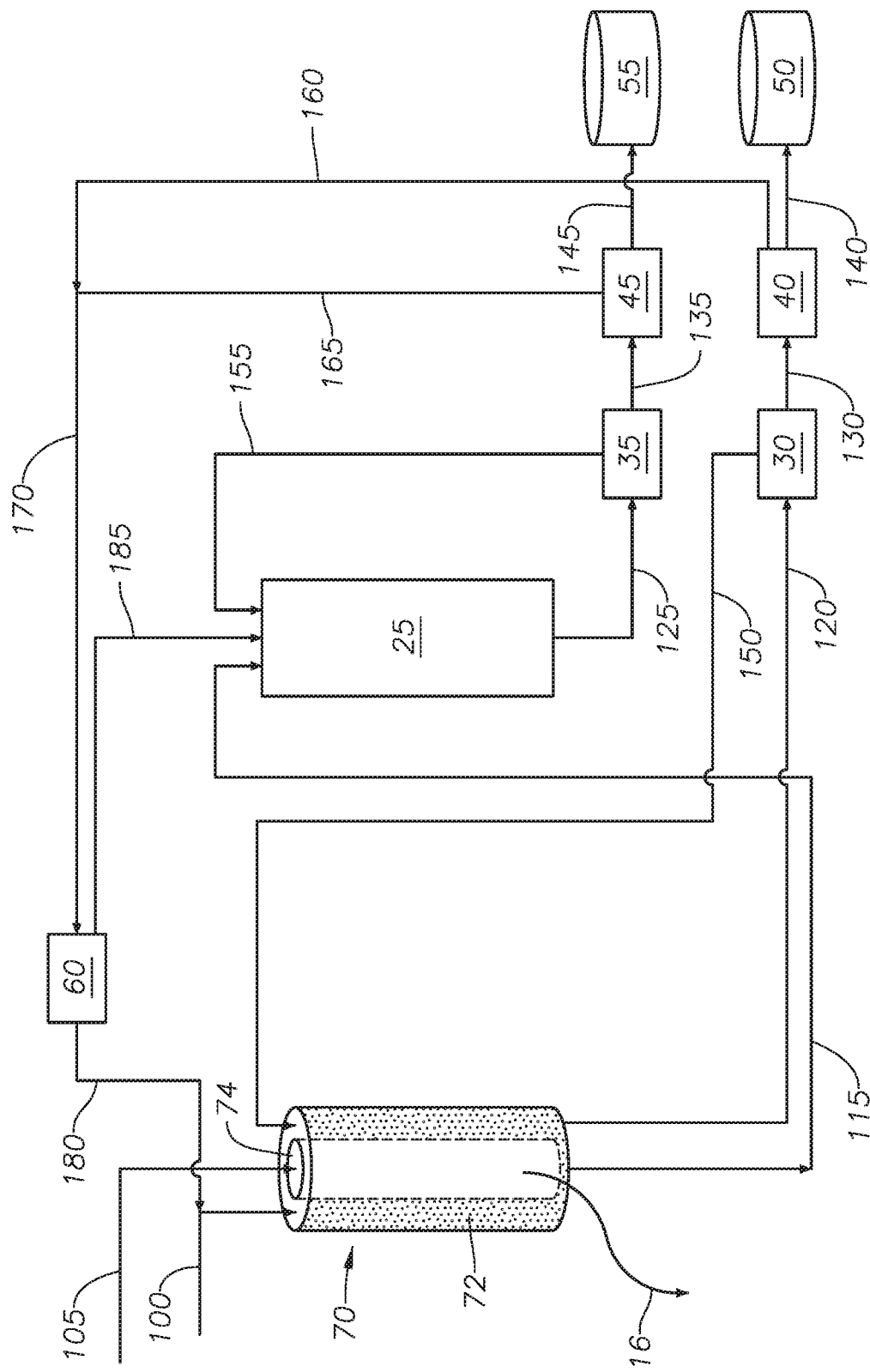
FIG. 3 provides a process flow diagram of an embodiment of the process.

Referring to FIG. 3 with reference to FIG. 2, an alternate embodiment of the method for separately producing butanols is described. Mixed butenes stream 100 can be introduced to shell side 72 of reaction membrane unit 70, along with TBA reactor water feed 180. Separation membrane unit 70 can include shell side 72, tube side 74, and membrane 16. Membrane 16 can be a cylinder defining a space extending through a longitudinal direction of membrane 16. Membrane 16 can define tube side 74, such that tube side 14 is enclosed within membrane 16 and can be the space defined by membrane 16. Membrane 16 and tube side 74 can extend the length of shell side 72. Shell side 72 can be an annulus defined by a wall of separation membrane unit 70 and the membrane 16, such that mixed butenes stream 100 can flow through the annulus.

Membrane 16 can be any type of membrane selective for one or more of the butenes in mixed butenes stream. Membrane 16 can allow selective gases to permeate. The selective gases can include 1-butene, alternately 1-butene and 2-butene, and alternately isobutene. In at least one embodiment, membrane 16 is selective for 1-butene and the selective gases includes 1-butene. In at least one embodiment, membrane 16 is selective for 2-butene and the selective gases includes 2-butene. In at least one embodiment, membrane 16 is selective for both 1-butene and 2-butene and the selective gases includes 1-butene and 2-butene. In at least one embodiment, membrane 16 is selective for isobutene and the selective gases includes isobutene. Membrane 16 can include a membrane composed of any material with the ability to separate 1-butene and 2-butene from isobutene. Examples of membranes for use in membrane 16 an include mineral membranes, carbon membranes, zeolite membranes, and polymer-based membranes. Membrane materials can include titanium dioxide, aluminum oxide, CaA, MFI-zeolite, polymers containing bis-phenyl-9,9-fluorene group. Membranes suitable for use in membrane 16 can be made of membrane materials or coated with suitable membrane materials. In reaction membrane unit 70, the selective gases in mixed butenes stream 100 can permeate from shell side 72 through membrane 16 to tube side 76.

Sweep gas 105 can be introduced to tube side 74 of reaction membrane unit 70. The selective gases that permeate to tube side 74 can be collected in sweep gas 105 and exit reaction membrane unit 70 as permeate stream 115. The temperature of tube side 74 in reaction membrane unit 70 can be between 5 deg C. and 160 deg C. Permeate stream 115 can be introduced to SBA reactor 25 as described with reference to FIG. 2.

Shell side 72 can be packed with the TBA catalyst. The butene gases in mixed butenes 100 that do not permeate through membrane 16 can remain on shell side 72. The butene gases on shell side 72 can react with water in the presence of the TBA catalyst to produce tert-butanol. Shell side 72 of reaction membrane unit 70 can be operated at a TBA reaction temperature. The TBA reaction temperature can be between 5 deg C. and 120 deg C. The pressure on the retentate side of reaction membrane unit 70, shell side 72, can be between 0.1 MPa and 10 MPa and alternately between 0.1 MPa and 7 MPa. The pressure on the permeate side of reaction membrane unit 70, tube side 74, can be between 0.01 MPa and 5 MPa and alternately between 0.1 MPa and 3 MPa. The pressure on the retentate side of reaction membrane unit 70 can be greater than the pressure on the permeate side. The residence time through reaction membrane unit 70 can be between 0.01 hours and 20 hours.

The temperature in reaction membrane unit 70 can be controlled by heating elements positioned adjacent to the exterior of reaction membrane unit 70. Temperature in reaction membrane unit 70 can be maintained by heating one or more of the feed streams to the reaction membrane unit 70.

TBA reactor effluent 120 can exit shell side 72 of reaction separation unit 70. TBA reactor effluent 120 can be introduced to TBA gases splitter 30 as described with reference to FIG. 2. Unreacted butenes stream 150 can be recycled to shell side 72 of reaction membrane unit 70.

Figure 4:
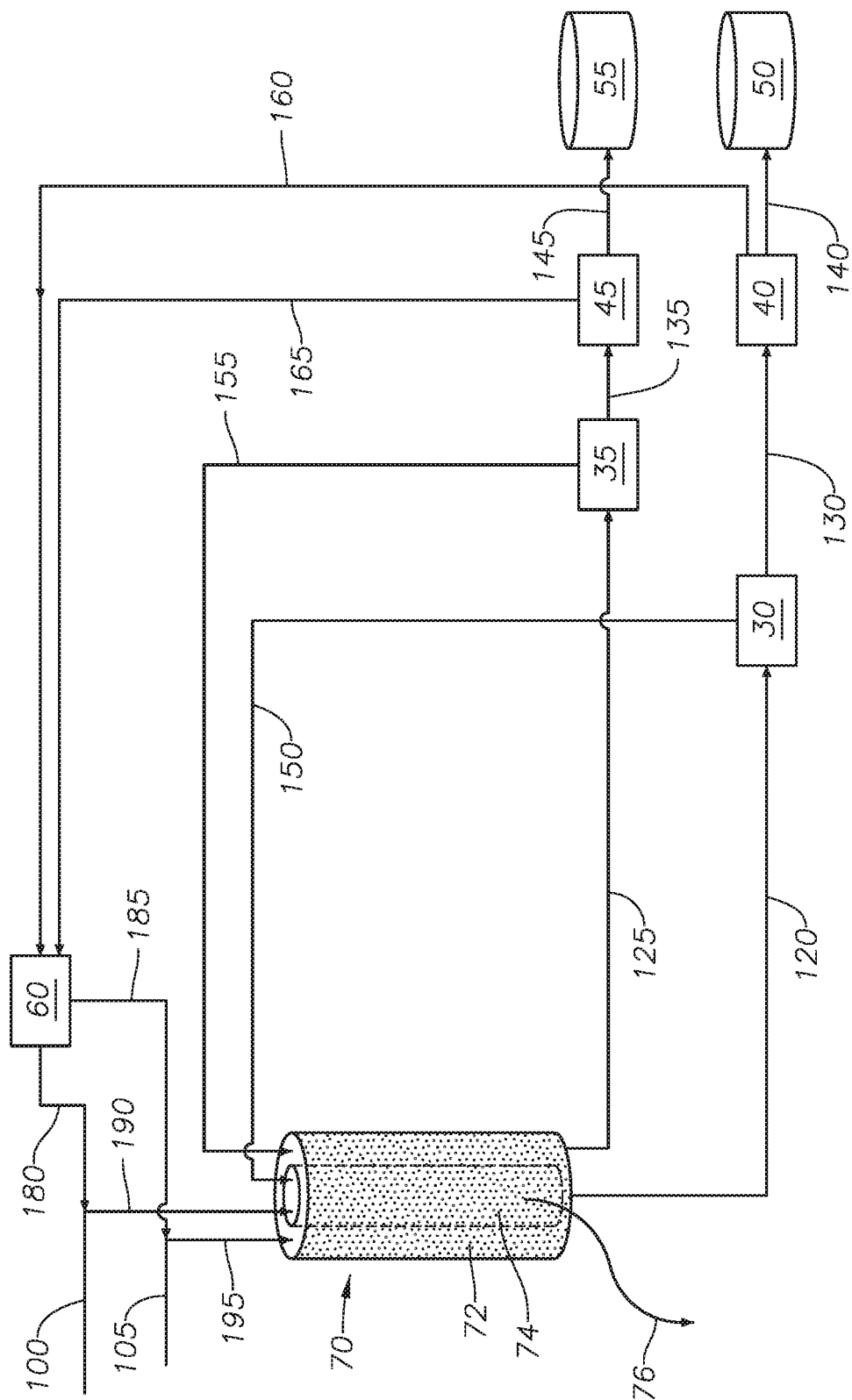
FIG. 4 provides a process flow diagram of an embodiment of the process.

Referring to FIG. 4 and with reference to FIGS. 2 and 3, an embodiment of the method and apparatus for separately producing tert-butanol and sec-butanol is provided. Mixed butenes stream 100 is introduced to tube side 74 of reaction membrane unit 70 along with TBA reactor water feed 180. In at least one embodiment, mixed butenes stream 100 and TBA reactor water feed 180 can be mixed upstream of reaction membrane unit 70 to produce mixed tube feed stream 190 and mixed tube feed stream 190 can be introduced to tube side 74. SBA reactor water feed 185 can be introduced to shell side 72 of reaction membrane unit 70. In at least one embodiment, sweep gas 105 can be introduced to shell side 72. In at least one embodiment, sweep gas 105 and SBA reactor water feed 185 can be mixed upstream of reaction membrane unit 70 to produce mixed shell feed stream 195 and mixed shell feed stream 195 can be introduced to shell side 72 of reaction membrane unit 70. In at least one embodiment, reaction membrane unit 70 is in the absence of sweep gas 105.

Both tube side 74 and shell side 72 can include a catalyst. Tube side 74 can include a TBA catalyst. Shell side 72 can include a SBA catalyst.

The selective gases can permeate membrane 76 from tube side 74 to shell side 72. The selective gases can react with water in the presence of the SBA catalyst in shell side 72 to produce sec-butanol. Shell side 72 can be operated at an SBA reaction temperature between 80 deg C. and 250 deg C. The retentate gases can react with water in the presence of the TBA catalyst in tube side 74 to produce tert-butanol. Tube side 74 can be operated at a TBA reaction temperature between 5 deg C. and 120 deg C.

The sec-butanol, along with water and the unreacted selective gases can be collected as SBA reactor effluent 125 and introduced to SBA gases splitter 35 as described with reference FIGS. 2 and 3. In embodiments where sweep gas 105 is introduced to shell side 72, SBA reactor effluent 125 can also include the sweep gas.

The tert-butanol, along with water and the unreacted retentate gases can be collected as TBA reactor effluent 120 and introduced to TBA gases splitter 30 as described with reference to FIGS. 2 and 3. Unreacted gases stream 155 can be recycled to shell side 72 of reaction membrane unit 70. Advantageously, the embodiment described with reference to FIG. 3 has reduced complexity and therefore increased operating efficiency due to the absence of two reactors downstream of the membrane unit.

Additional equipment, such as storage tanks, can be used to contain the feeds to each unit. Instrumentation can be included on the process lines to measure various parameters, including temperatures, pressures, and flow rates.

In at least one embodiment, both the SBA reactor and the TBA reactor are in the absence of membranes.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

There various elements described can be used in combination with all other elements described here unless otherwise indicated.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed here as from about one particular value to about another particular value and are inclusive unless otherwise indicated. When such a range is expressed, it is to be understood that another embodiment is from the one particular value to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these references contradict the statements made here.

As used here and in the appended claims, the words "comprise," "has," and "include" and all grammatical variations thereof are each intended to have an open, non-limiting meaning that does not exclude additional elements or steps.

That which is claimed is:

1. A system of separately producing tert-butanol and sec-butanol, the system comprising:
    a reaction membrane unit, the reaction membrane unit comprising:
        a membrane, the membrane configured to allow selective gases in a mixed butenes stream to permeate through from a tube side of the membrane to a shell side of the membrane, wherein retentate gases remain on the tube side of the membrane, wherein the mixed butenes stream comprises butene gases,
        the tube side of the membrane, defined by the membrane such that the tube side is enclosed within the membrane, the tube side comprising a TBA catalyst, wherein the tube side operates at a SBA reaction temperature, wherein the retentate gases react with water in a TBA reactor water feed in the presence of the TBA catalyst to produce tert-butanol, wherein the retentate gases comprise isobutene, wherein the tert-butanol exits the tube side as a TBA reactor effluent; and
        the shell side of the membrane, the shell side comprising an SBA catalyst, wherein the selective gases react with water in an SBA reactor water feed in the presence of the SBA catalyst to produce sec-butanol, wherein the shell side operates at an SBA reaction temperature, wherein the selective gases are selected from the group consisting of 1-butene, 2-butene, and combinations of the same, wherein the sec-butanol is collected by a sweep gas to produce a SBA reactor effluent, wherein the sweep gas is selected from the group consisting of nitrogen, argon, other noble gases, and combinations of the same.

2. The system of claim 1, further comprising:
    a SBA gases splitter fluidly connected to the shell side of the membrane of the reaction membrane unit, wherein the SBA gases splitter is configured to separate unreacted gases from the SBA reactor effluent to produce an unreacted gases stream and a separated liquids stream; and
    a SBA liquid separator fluidly connected to the SBA gases splitter, wherein the SBA liquid separator is configured to separate water from the separated liquids stream to produce a separated water stream and an SBA product stream.

3. The system of claim 1, further comprising:
    a TBA gases splitter fluidly connected to the tube side of the membrane of the reaction membrane unit, wherein the TBA gases splitter is configured to separate unreacted butenes from the TBA reactor effluent to produce an unreacted butenes stream and a separated liquids stream; and
    a TBA liquid separator fluidly connected to the TBA gases splitter, wherein the TBA liquid separator is configured to separate water from the separated liquids stream to produce a recycled water stream and a TBA product stream.

4. The system of claim 1, wherein the SBA catalyst is selected from the group consisting of organic acids, inorganic acids, and solid acids.

5. The system of claim 1, wherein the TBA catalyst is selected from the group consisting of organic acids, inorganic acids, and solid acids.

6. The system of claim 1, wherein the SBA reaction temperature is between 80 deg C. and 250 deg C.

7. The system of claim 1, wherein the TBA reaction temperature is between 5 deg C. and 120 deg C.

8. A system of separately producing tert-butanol and sec-butanol, the system comprising:
    a reaction membrane unit, the reaction membrane unit comprising:
        a membrane, the membrane configured to allow selective gases in a mixed butenes stream to permeate through from a shell side of the membrane to a tube side of the membrane, wherein retentate gases remain on the shell side of the membrane, wherein the mixed butenes stream comprises butene gases,
        the shell side of the membrane, the shell side comprising a TBA catalyst, wherein the shell side operates at a TBA reaction temperature, wherein the retentate gases react with water in a TBA reactor water feed in the presence of the TBA catalyst to produce tert-butanol, wherein the retentate gases comprise isobutene, wherein the tert-butanol exits the shell side as a TBA reactor effluent, and
        the tube side of the membrane, defined by the membrane such that the tube side is enclosed within the membrane, wherein the selective gases are selected from the group consisting of 1-butene, 2-butene, and combinations of the same, wherein the selective gases are collected by a sweep gas to produce a permeate stream, wherein the sweep gas is selected from the group consisting of nitrogen, argon, other noble gases, and combinations of the same; and
    a sec-butanol (SBA) reactor fluidly connected to the tube side of the membrane, the SBA reactor comprising an SBA catalyst, wherein the selective gases in the permeate stream react with water from a SBA reactor water feed in the presence of the SBA catalyst to produce sec-butanol, wherein the sec-butanol exits the SBA reactor as a SBA reactor effluent, wherein the SBA reactor operates at a SBA reaction temperature.

9. The system of claim 8, further comprising:
a SBA gases splitter fluidly connected to the SBA reactor, wherein the SBA gases splitter is configured to separate unreacted gases from the SBA reactor effluent to produce an unreacted gases stream and a separated liquids stream; and
a SBA liquid separator fluidly connected to the SBA gases splitter, wherein the SBA liquid separator is configured to separate water from the separated liquids stream to produce a separated water stream and an SBA product stream.

10. The system of claim 8, further comprising the steps of:
a TBA gases splitter fluidly connected to the tube side of the membrane of the reaction membrane unit, wherein the TBA gases splitter is configured to separate unreacted butenes from the TBA reactor effluent to produce an unreacted butenes stream and a separated liquids stream; and
a TBA liquid separator fluidly connected to the TBA gases splitter, wherein the TBA liquid separator is configured to separate water from the separated liquids stream to produce a recycled water stream and a TBA product stream.

11. The system of claim 8, wherein the SBA catalyst is selected from the group consisting of organic acids, inorganic acids, and solid acids.

12. The system of claim 8, wherein the TBA catalyst is selected from the group consisting of organic acids, inorganic acids, and solid acids.

13. The system of claim 8, wherein the SBA reaction temperature is between 80 deg C. and 250 deg C.

14. The system of claim 8, wherein the TBA reaction temperature is between 5 deg C. and 120 deg C.

15. A system for separately producing sec-butanol and tert-butanol, the system comprising:
a separation membrane unit, the separation membrane unit comprising:
a membrane, the membrane configured to allow selective gases in a mixed butenes stream to permeate through from a shell side of the membrane to a tube side of the membrane, wherein retentate gases remain on the shell side of the membrane, wherein the mixed butenes stream comprises butene gases,
the shell side of the membrane, wherein the retentate gases comprise isobutene, wherein the retentate gases exit the shell side as a retentate stream, and
the tube side of the membrane, defined by the membrane such that the tube side is enclosed within the membrane, wherein the selective gases are selected from the group consisting of 1-butene, 2-butene, and combinations of the same, wherein the selective gases are collected by a sweep gas to produce a permeate stream, wherein the sweep gas is selected from the group consisting of nitrogen, argon, other noble gases, and combinations of the same;
a tert-butanol (TBA) reactor fluidly connected to the shell side of the membrane, the TBA reactor comprising a TBA catalyst, wherein the retentate gases in the retentate stream react with water from a TBA reactor water feed in the presence of the TBA catalyst to produce tert-butanol, wherein the tert-butanol exits the TBA reactor as a TBA reactor effluent, wherein the TBA reactor operates at a TBA reaction temperature; and
a sec-butanol (SBA) reactor fluidly connected to the tube side of the membrane, the SBA reactor comprising an SBA catalyst, wherein the selective gases in the permeate stream react with water from a SBA reactor water feed in the presence of the SBA catalyst to produce sec-butanol, wherein the sec-butanol exits the SBA reactor as a SBA reactor effluent, wherein the SBA reactor operates at a SBA reaction temperature.

16. The system of claim 15, further comprising:
a SBA gases splitter fluidly connected to the SBA reactor, wherein the SBA gases splitter is configured to separate unreacted gases from the SBA reactor effluent to produce an unreacted gases stream and a separated liquids stream; and
a SBA liquid separator fluidly connected to the SBA gases splitter, wherein the SBA liquid separator is configured to separate water from the separated liquids stream to produce a separated water stream and an SBA product stream.

17. The system of claim 15, further comprising the steps of:
a TBA gases splitter fluidly connected to the TBA reactor, wherein the TBA gases splitter is configured to separate unreacted butenes from the TBA reactor effluent to produce an unreacted butenes stream and a separated liquids stream; and
a TBA liquid separator fluidly connected to the TBA gases splitter, wherein the TBA liquid separator is configured to separate water from the separated liquids stream to produce a recycled water stream and a TBA product stream.

18. The system of claim 15, wherein the SBA catalyst is selected from the group consisting of organic acids, inorganic acids, and solid acids.

19. The system of claim 15, wherein the TBA catalyst is selected from the group consisting of organic acids, inorganic acids, and solid acids.

20. The system of claim 15, wherein the SBA reaction temperature is between 80 deg C. and 250 deg C. and wherein the TBA reaction temperature is between 5 deg C. and 120 deg C.

* * * * *